United States Patent [19]

Bolanos et al.

[11] Patent Number: 5,690,269
[45] Date of Patent: Nov. 25, 1997

[54] ENDOSCOPIC STAPLER

[75] Inventors: Henry Bolanos, East Norwalk; Charles R. Sherts, Southport; Thomas A. Pelletier, Wallingford, all of Conn.

[73] Assignee: United States Surgical Corporation, Norwalk, Conn.

[21] Appl. No.: 640,589

[22] Filed: May 1, 1996

Related U.S. Application Data

[63] Continuation of Ser. No. 415,776, Mar. 31, 1995, Pat. No. 5,540,375, which is a continuation of Ser. No. 49,881, Apr. 20, 1993, abandoned.

[51] Int. Cl.$^6$ ............................................. A61B 17/068
[52] U.S. Cl. ...................... 227/176.1; 227/19; 227/178.1
[58] Field of Search ................................. 227/19, 175.1, 227/176.1, 178.1

[56] References Cited

U.S. PATENT DOCUMENTS

| | | |
|---|---|---|
| Re. 28,932 | 8/1976 | Noiles et al. . |
| 4,122,989 | 10/1978 | Kapitanov et al. . |
| 4,127,227 | 11/1978 | Green . |
| 4,206,863 | 6/1980 | Savino . |
| 4,232,810 | 11/1980 | Russell . |
| 4,305,539 | 12/1981 | Korolkov et al. .......... 227/19 |
| 4,345,600 | 8/1982 | Rothfuss . |
| 4,520,817 | 6/1985 | Green . |
| 4,665,916 | 5/1987 | Green . |
| 4,749,114 | 6/1988 | Green . |
| 4,773,420 | 9/1988 | Green . |
| 4,821,939 | 4/1989 | Green . |
| 4,978,049 | 12/1990 | Green . |
| 5,030,226 | 7/1991 | Green et al. . |
| 5,040,715 | 8/1991 | Green et al. . |
| 5,059,201 | 10/1991 | Asnis . |
| 5,071,430 | 12/1991 | De Salis et al. . |
| 5,084,057 | 1/1992 | Green et al. . |
| 5,100,420 | 3/1992 | Green et al. . |
| 5,116,349 | 5/1992 | Aranyi . |
| 5,158,567 | 10/1992 | Green . |
| 5,188,636 | 2/1993 | Fedotov . |
| 5,242,457 | 9/1993 | Akopov et al. . |
| 5,364,003 | 11/1994 | Williamson, IV . |
| 5,425,737 | 6/1995 | Burbank et al. . |
| 5,540,375 | 7/1996 | Bolanos et al. . |

FOREIGN PATENT DOCUMENTS

| | | |
|---|---|---|
| 327325 | 8/1989 | European Pat. Off. . |
| 541987 | 5/1993 | European Pat. Off. . |
| 728848 | 5/1980 | U.S.S.R. . |
| 885898 | 1/1962 | United Kingdom . |

*Primary Examiner*—Scott A. Smith

[57] ABSTRACT

An endoscopic or laparoscopic surgical instrument for applying fasteners to bodily tissue is disclosed. The instrument includes a handle assembly, an endoscopic portion and a jaw portion. The instrument is configured and dimensioned to be insertable through a cannula, and is useful for applying a purse string to bodily tissue.

6 Claims, 11 Drawing Sheets

ENDOSCOPIC STAPLER

This is a continuation of U.S. Serial application Ser. No. 08/415,776 filed Mar. 31, 1995 now U.S. Pat. No. 5,540,375 which is a continuation of U.S. application Ser. No. 08/049,881 filed Apr. 20, 1993 now abandoned.

BACKGROUND OF THE INVENTION

1. Field of the Invention

The present invention relates to surgical staplers and, more particularly to surgical staplers for use in endoscopic and laparoscopic procedures.

2. Discussion of the Prior Art

Laparoscopic and endoscopic surgical procedures are minimally invasive procedures in which operations are carried out within the body by means of elongated instruments inserted through small entrance openings in the body. The initial opening in the body tissue to allow passage of the endoscopic or laparoscopic instruments to the interior of the body may be a natural passageway of the body, or it can be created by a tissue piercing instrument such as a trocar. With the aid of a cannula assembly inserted into the opening, laparoscopic or endoscopic instrumentation may then be used to perform desired surgical procedures.

Laparoscopic and endoscopic surgical procedures generally require that any instrumentation inserted in the body be sealed, i.e. provisions must be made to ensure that gases do not enter or exit the body through the instrument or the entrance incision so that the surgical region of the body, e.g. the peritoneum, may be insufflated. Mechanical actuation of such instruments is for the most part constrained to the movement of the various components along a longitudinal axis with means provided to convert longitudinal movement to lateral movement where necessary. Because the endoscopic or laparoscopic tubes, instrumentation, and any required punctures or incisions are relatively narrow, endoscopic or laparoscopic surgery is less invasive and causes much less trauma to the patient as compared to procedures in which the surgeon is required to cut open large areas of body tissue.

Surgical fasteners or staples are often used to join body tissue during laparoscopic and endoscopic procedures. Such fasteners can have a pair of legs joined by a backspan and are typically set into the body by means of an elongated instrument which crimps the fastener legs to secure the fastener and tissue.

Various types of stapling instruments have been known for fixing staples to body tissue. Generally, the staples have been applied by using instruments having an anvil and an ejector mechanism for driving the legs of a staple through the tissue and against the anvil for deforming the legs into a "B" shape or the like. An example of such a stapler having an anvil is disclosed in U.S. Pat. No. 4,665,916. An example of a surgical stapler having an anvil and adapted for endoscopic use is disclosed in U.S. Pat. No. 5,040,715. Although these and other various types of instruments are useful for driving the legs of the staple through tissue, there are times when it is not desirable, necessary or practical to drive the legs of the staple through the body tissue in order to affix a staple. For example, when applying a purse string to tissue, as in an end to end anastomosis procedure, it is not desirable or necessary to staple through tissue, but to affix the staples to the tissue.

In cases where a purse string is to be applied to a tubular section of tissue, known stapling instruments have been rather cumbersome and complex in order to provide an anvil against which the staples can be deformed. See, for example, U.S. Pat. Nos. 4,749,114 and 4,773,420. An anvilless surgical stapler for use in open surgery and a method of affixing a staple to tissue without completely piercing the tissue is disclosed in U.S. Pat. No. 4,821,939 and is incorporated herein by reference. While this anvilless stapler has found success in applying purse strings in open surgery, such a stapler is not properly configured and dimensioned to be used in endoscopic or laparoscopic procedures.

Accordingly, there is a need for an endoscopic surgical stapler adapted for use in confined areas. There is also a need for an anvilless surgical stapler capable of endoscopically applying staples to body tissue. There is also a need for an endoscopic surgical stapler for applying a purse string to body tissue. Additionally, there is a need for an endoscopic surgical stapling instrument capable of applying a purse string to body tissue, wherein the staples secure the string element to body tissue without piercing the tissue with the legs of the staples.

SUMMARY OF THE INVENTION

The present invention provides a novel anvilless endoscopic or laparoscopic surgical instrument having an endoscopic portion with proximal and distal end portions. In one embodiment, the instrument has a pair of jaws positioned at the distal end portion, each adapted to carry a fastener cartridge. The fastener cartridge has a tissue contacting surface and a plurality of fasteners slidably disposed therein. Both the endoscopic portion and the jaws are adapted to be insertable into a cannula. Each fastener has a pair of deformable legs joined by a backspan and are disposed within and ejected from the cartridge in a manner substantially similar to that disclosed in U.S. Pat. Nos. 4,821,939 and 5,158,567. Means for ejecting the fasteners may include at least one fastener firing cam member for contacting pushers disposed within the cartridge, the pushers being designed to contact and eject the fasteners from the cartridge. Means remote from the distal portion of the endoscopic instrument are adapted to cause the firing cam member to be drawn across the pusher members. This operation may be accomplished, for example, by having a slidable member disposed at the proximal end of the instrument which is attached to the cam member by means of a wire, a rod, or the like.

The purse string suture portion can be positioned adjacent the jaws and/or the tissue contacting surface of the fastener cartridge such that upon ejection of the fasteners, the suture will be held between the fastener backspans and tissue. A handle assembly having a stationary handle and a movable handle is also provided to open and close the fastener jaws.

In operation, a cannula is inserted into the abdominal cavity. The surgical instrument of the present invention is inserted through the cannula with the jaws in a substantially closed position. After insertion, the movable handle is moved away from the stationary handle thereby causing the jaws at the distal end of the instrument to open. The organ or tissue to which the purse string is to be applied is then oriented between the jaws. The movable handle is then brought into approximation with the stationary handle to cause the jaws to close about the organ or tissue. The purse string may then be applied by causing the fasteners to be ejected from the jaws, such as by causing a cam member to sequentially eject the fasteners from the cartridge, which thereby secures the suture in a purse string configuration about the organ or tissue. After firing, the jaws may then be opened to release the tissue or organ by moving the movable handle away from the stationary handle. After re-closing the jaws, the instrument may be withdrawn from the cannula. Finally, the purse string may be tightened about the organ or tissue by manipulating the suture as desired.

BRIEF DESCRIPTION OF THE DRAWINGS

The foregoing objects and other features of the invention will become more readily apparent and may be understood by referring to the following detailed description of illustrative embodiments of the endoscopic or laparoscopic surgical apparatus for applying a purse string, taken in conjunction with the accompanying drawings, in which.

DETAILED DESCRIPTION OF THE PREFERRED EMBODIMENTS

Figure 1:
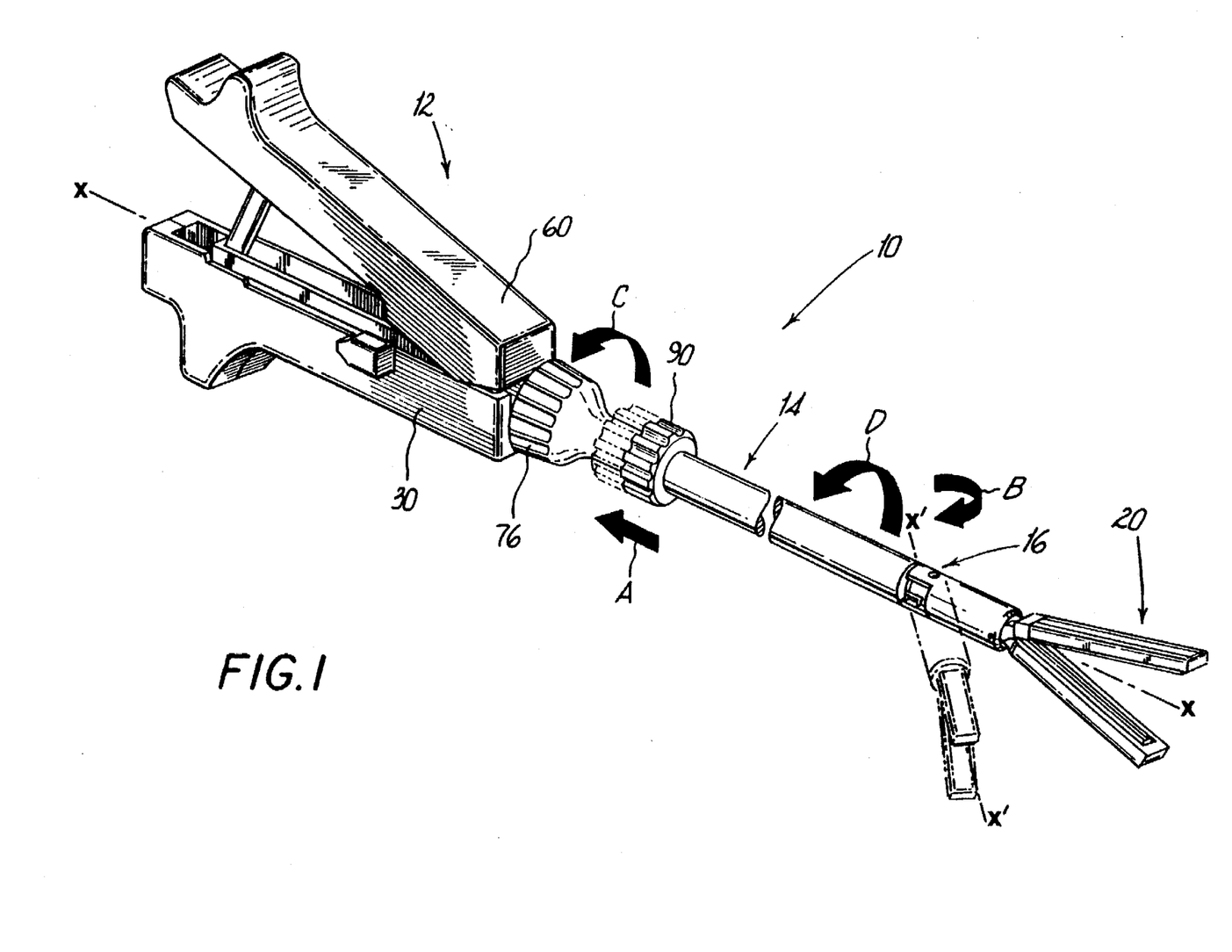
FIG. 1 illustrates a perspective view of a preferred embodiment of the present invention.

Referring now in specific detail to the drawings, in which like reference numerals identify similar or identical elements, FIG. 1 illustrates a first embodiment of the endoscopic or laparoscopic surgical apparatus 10 for applying surgical fasteners. Apparatus 10 comprises endoscopic portion 14, handle assembly 12 and fastener applying assembly 20. Endoscopic portion 14 and assembly 20 are configured and dimensioned to be inserted into a cannula. Handle assembly 12 is positioned at the proximal end of endoscopic portion 14 and is shown with stationary handle 30 and movable handle 60 in an open position. Handle assembly 12 functions to open and close assembly 20, which is positioned at the distal end of endoscopic portion 14. As shown by arrows A and B, and as will be described in further detail below, endoscopic portion 14 can be articulated at articulation joint 16 by manipulating articulation knob 90. Proximal movement of knob 90 will cause the distal end of endoscopic portion 14 and assembly 20, shown in phantom, to deflect at joint 16 away from the instrument's central axis X—X. Arrows C and D depict rotational movement of the endoscopic and distal portions of instrument 10 which can be achieved by rotating knob 76.

Figure 2:
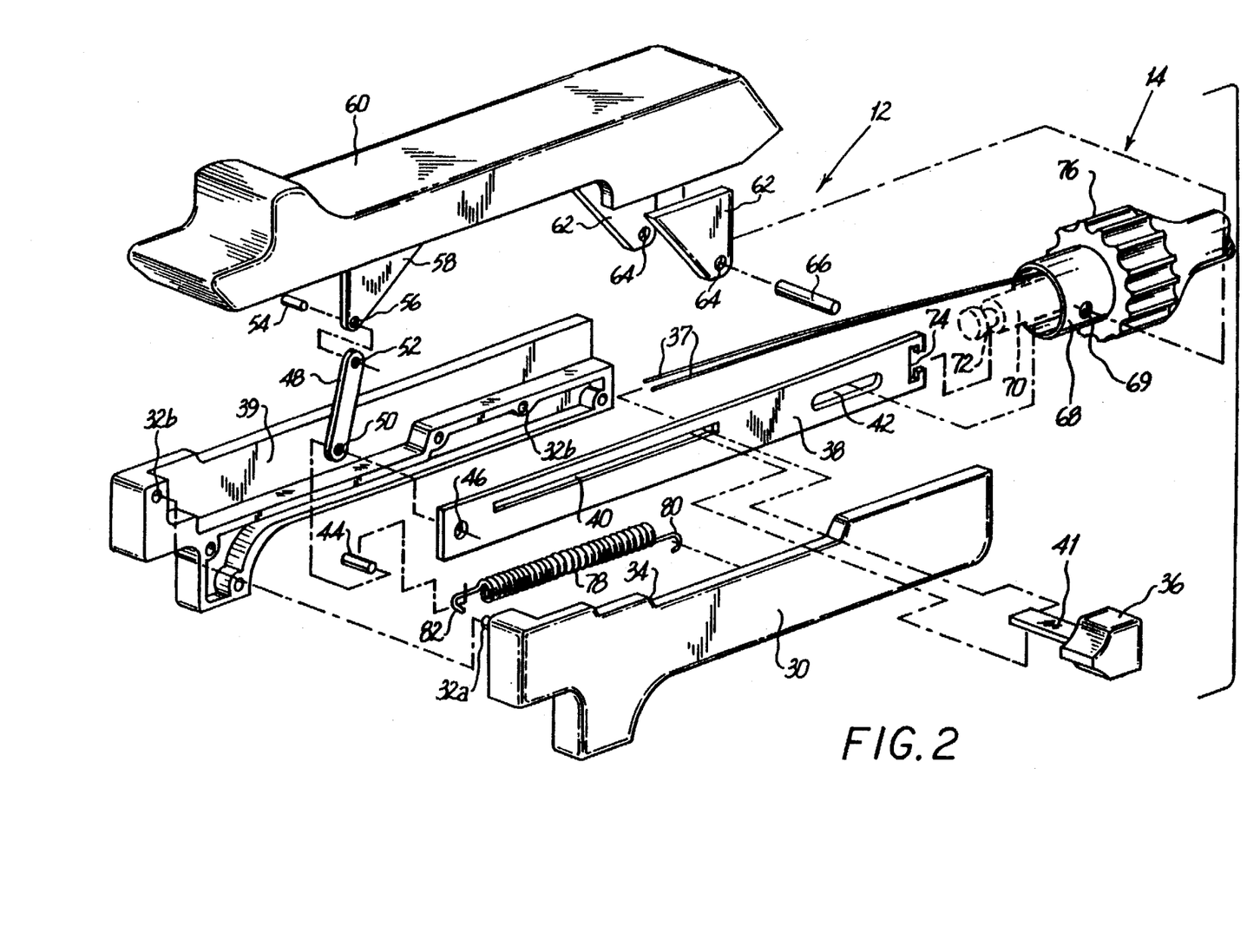
FIG. 2 illustrates an exploded view of the handle assembly of FIG. 1.

Turning to handle assembly 12 with reference to FIG. 2, stationary handle housing 30 is shown in two halves. Halves 30 can be secured together by mating protrusions 32a with corresponding recesses 32b. When joined, the stationary housing defines recess 39 wherein proximal plate 38 is longitudinally movable. Plate 38 includes firing slot 40, pin opening 46, distal slot 42 and center rod opening 74. Firing slot 40 permits tongue 41 of firing button 36 to be slidably received therein. Tongue 41 is further connected to firing wires 37, the purpose of which will be described in greater detail below.

Link 48 serves to connect the proximal end of movable handle 60 with plate 38. Plate pin 44 is insertable through pin opening 46 in plate 38 and lower pin opening 50 in link 48. Movable handle pin 54 is insertable through upper pin opening 52 in link 48 and pin opening 56 in movable handle link connector plate 58. The distal end of movable handle 60 is pivotally secured to rear cover tube 68 by handle pivot pin 66. Handle pivot pin 66 passes through pivot pin openings 64 in pivot plates 62 and pin openings 69 in rear cover tube 68. The distal end of plate 38 is insertable into rear cover tube 68 and is slidable therein by means of slot 42 through which pin 66 passes. The proximal end of endoscopic portion 14 is rotatably secured to rear cover tube 68 and inner rod 70 (shown in phantom) of endoscopic portion 14 has axial groove 72 which is insertable into slot 74 of plate 38. When assembled, inner rod 70 will be disposed distal of pin 66.

In operation, when movable handle 60 is urged towards stationary handle 30, the distal end of movable handle 60 pivots about pin 66, causing link 48 to urge plate 38 in a distal direction. When closed, movable handle 60 remains adjacent stationary handle 30 due to over centering of pin 54. Distal movement of plate 38, causes inner rod 70 to move distally as well. Spring 78, disposed adjacent plate 38 is secured to stationary handle protrusion 81 (see FIG. 9) by distal spring hook 80 and secured to cam pin 44 by proximal spring hook 82. Spring 78 serves to provide resistance to the closing of the movable handle and to facilitate the opening of the movable handle.

Figure 3:
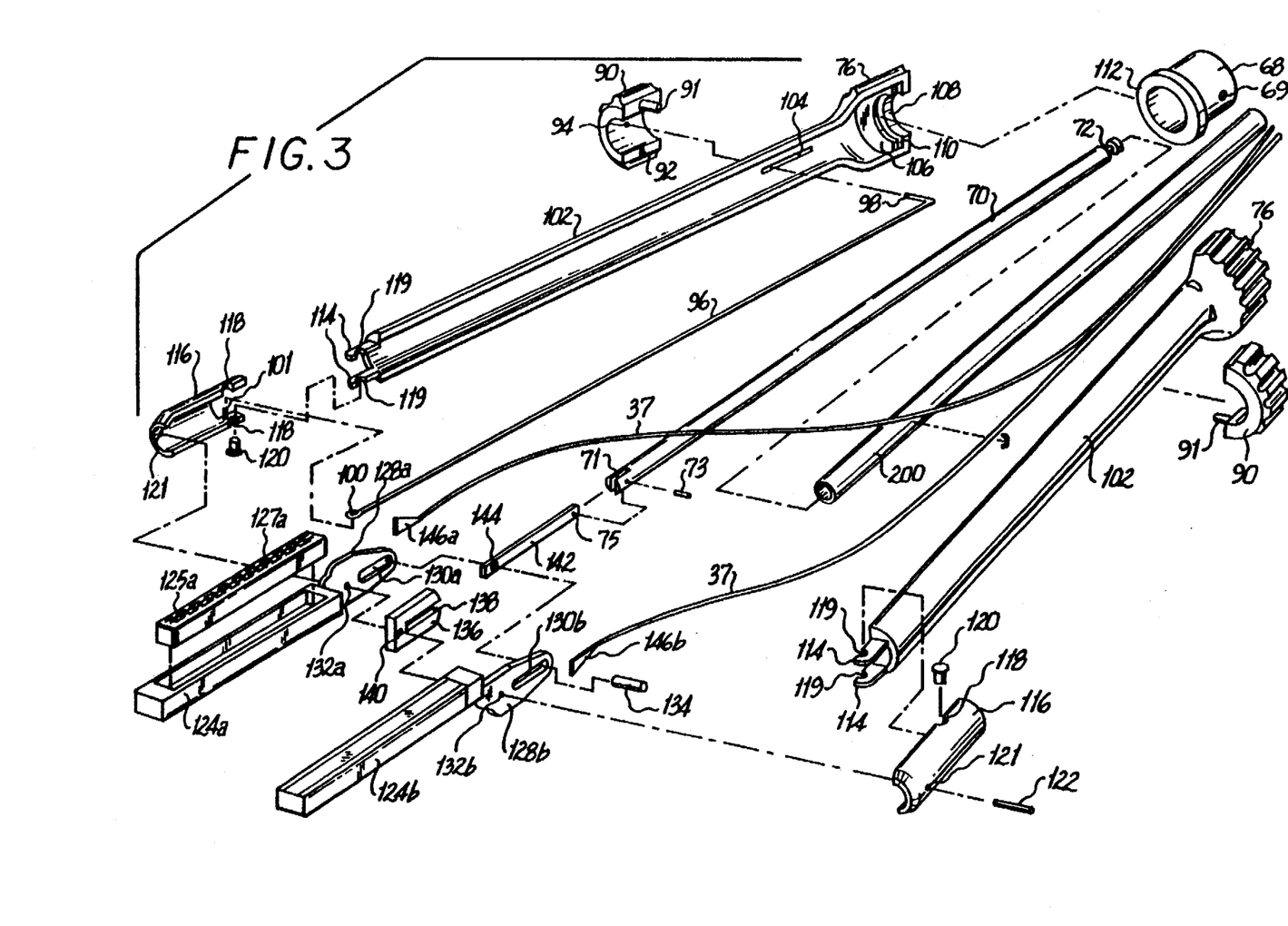
FIG. 3 illustrates an exploded view of the endoscopic and distal portions assembly of FIG. 1.

Turning to the endoscopic and distal portions of the surgical device of the present invention, with reference to FIGS. 1, 2 and 3, the endoscopic portion includes cover tube 102 (shown in two halves), inner rod 70, firing wires 37, articulation rod 96, and optional inner rod sheath 200. Proximal rotation knob 76 has an irregular outer surface to facilitate grasping and serves to allow the surgeon to rotate cover tube 102. Rotation knob 76 has inner circular disks 106 and 108 which define circular channel 110. Flange 112 of cover tube 68 is received within channel 110 in a manner which permits cover tube 102 to rotate with respect to rear cover tube 68 and, therefore, handle assembly 12.

The articulating mechanism includes articulating knob 90, rod 96 and articulating joint 16. Rod 96 has distal end 100 and proximal hook 98. Distal end 100 of articulating rod 96 is secured to articulating portion 116 by pin 101. The proximal end of rod 96 terminates in hook 98 which passes through slot 104 of lower tube 102 and is received within recess 94 of articulating knob 90. Articulating knob 90 is assembled about tube 102 by joining protrusions 91 and corresponding recesses 92. Hook 98, secured to the articulating knob at recess 94 and being slidable within slot 104 of tube 102, permits movement of the articulating knob along longitudinal axis X—X of endoscopic portion 14. Articulating portion 116 of endoscopic portion 14 is joined to cover tube 102 at joint 16. Opposing pins 120 are received within pin openings 118 of articulating portion 116 and pin openings 119 formed in articulating joint members 114. By moving articulating knob 90 longitudinally, articulating rod 96 is also moved longitudinally, thereby causing articulating portion 116 to pivot about pins 120 of articulation joint 16 in a direction away from the longitudinal axis X—X of endoscopic portion 14.

Figure 6:
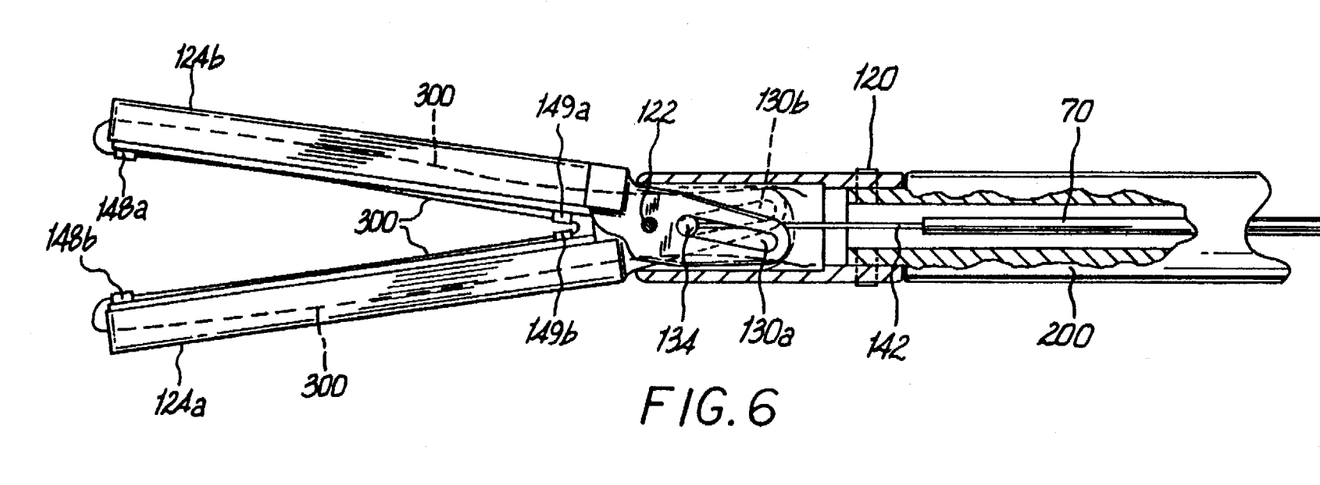
FIG. 6 illustrates a side elevation cut away of the jaws of FIG. 1 in an open position.
Figure 7:
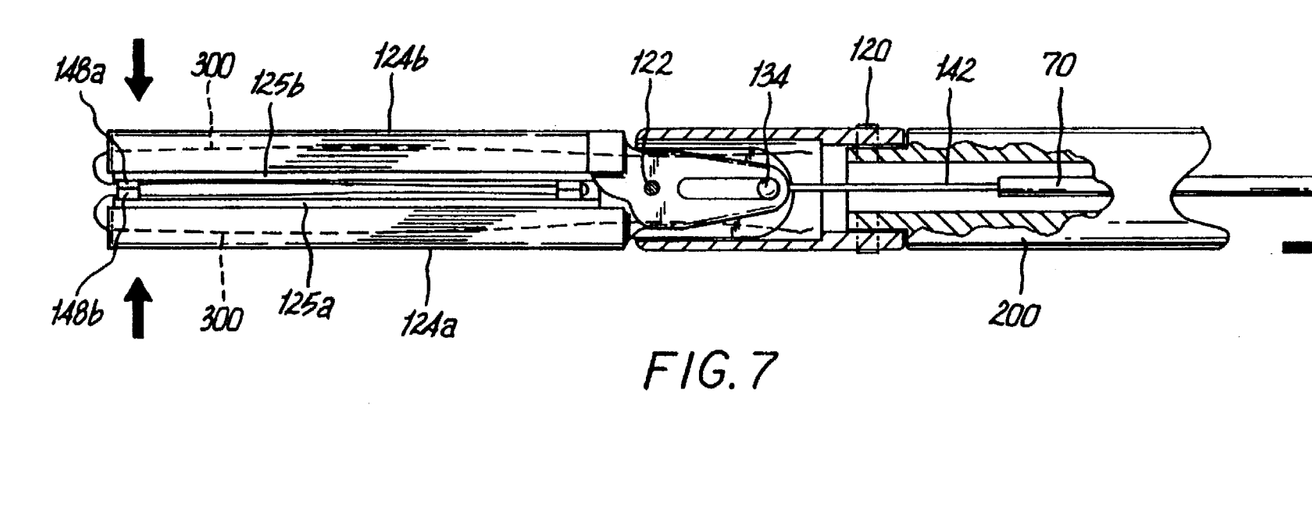
FIG. 7 illustrates the jaws of FIG. 6 in a closed position.

With reference to FIGS. 3, 6 and 7, fastener carrying cartridges 125a and 125b are disposed within jaws 124a and 124b and have tissue contacting surfaces 127a and 127b. Jaws 124 can be adapted to slidably receive cartridges 125 so as to provide means for reloading the instrument for multiple firings. Alternatively, the fasteners can be disposed directly into the jaws without the use of cartridges. Jaws 124 are secured to articulating portion 116 by pin 122. Pin 122 is received through pin openings 121 of articulating portion 116, pin openings 132a and 132b of jaw cam plates 128a and 128b and through pin opening 140 of jaw spacer 136. Jaw cam pin 134 passes through jaw cam slots 130a and 130b of jaw cam plates 128a and 128b, spacer slot 138 of jaw spacer 136 and pin opening 144 of articulating jaw cam plate 142. The proximal end of jaw cam plate 142 is secured to center rod 70 at recess 71 by pin 73 which passes through plate 142 at pin opening 75. Cam plate 142 is made of a flexible material to permit articulation and enable manipulation of the jaw camming mechanisms while the instrument is articulated.

Firing wires 37 are also disposed in endoscopic portion 14 and have firing cams 146a and 146b which are disposed within jaws 124a and 124b, respectively. Suture 300 is positioned adjacent tissue contacting surfaces 127 and jaws 124 (see FIGS. 6 and 7). Operation of the firing mechanism will be discussed in greater detail below. Optionally, inner rod sheath 200 can be provided to facilitate an alternate method of rotating the distal end of the instrument (see discussion of FIGS. 12 and 13 below).

Turning to the jaw manipulation mechanism of the present invention, with reference to FIGS. 3, 4, 6 and 7, when the jaws are in the open position, jaw pin 134 is disposed at the distal end of slots 130a and 130b. In this position, inner rod 70 is in a forward or distal position and movable handle 60 is in its open position. By closing the handle assembly, i.e. moving movable handle 60 toward stationary handle 30, inner rod 70 and jaw cam pin 134 are drawn in a proximal direction. When jaw cam pin 134 travels through jaw cam slots 130a and 130b, jaws 124a and 124b are caused to pivot about jaw pin 122 and are urged towards each other. When the instrument is not articulated, the jaws will move towards the longitudinal axis X—X of the instrument. If the instrument is articulated, the jaws will move towards articulated jaw axis X'—X'. As shown in FIG. 7, when the jaws are fully closed, jaw stops 148a, 148b, 149a and 149b are in contact and tissue contacting surfaces 127 of cartridges 125 are in substantial parallel alignment.

Figure 9:
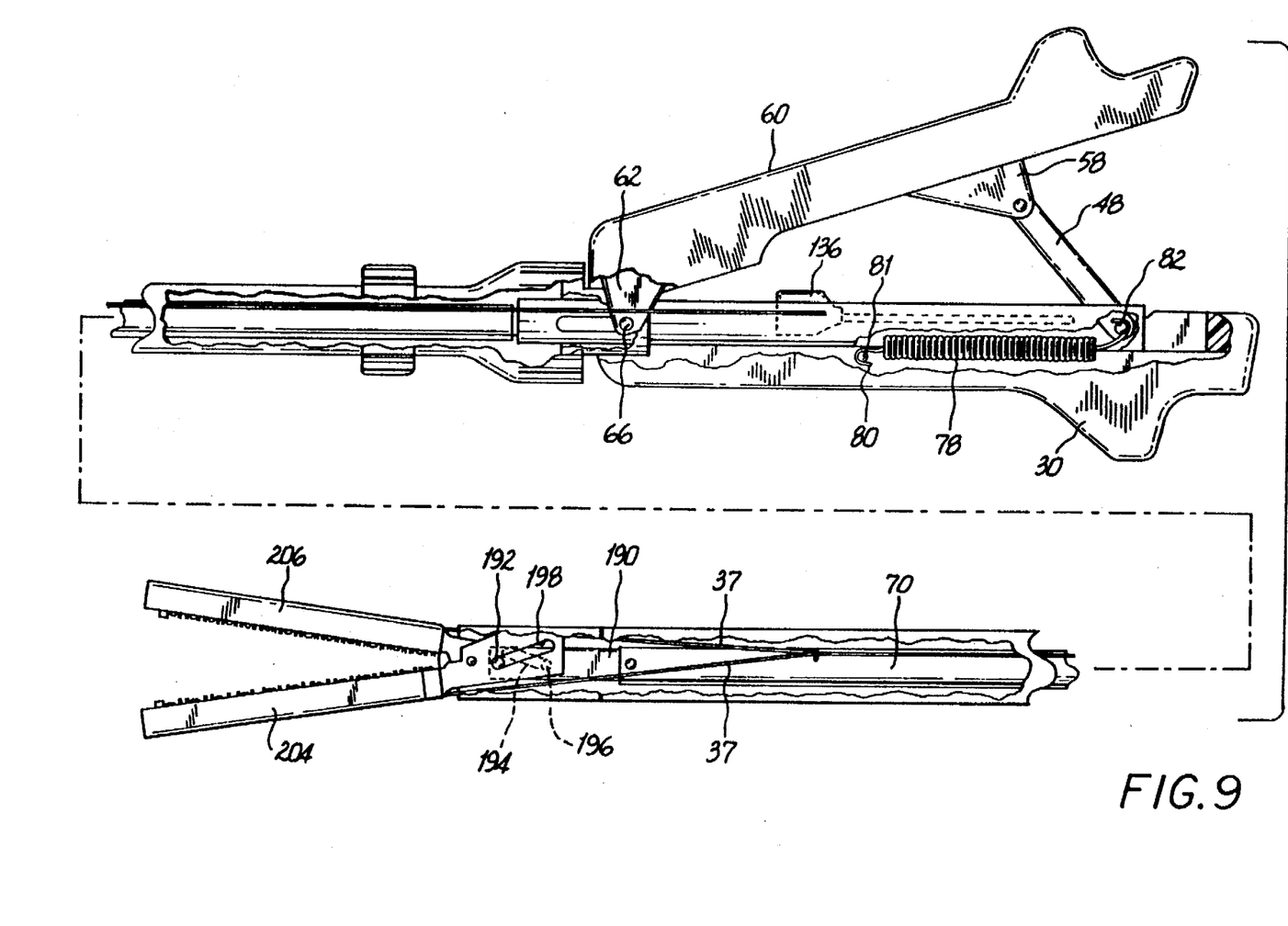
FIG. 9 illustrates a further alternative embodiment of the present invention.

An alternative method for closing the jaws is illustrated in FIG. 9. In this embodiment, articulating cam plate 190 has pin 192 which travels in slot 198 of jaw 204. Jaw 206 has pin 196 which is configured to travel along slot 194 of cam plate 190. When movable handle 60 is urged towards stationary handle 30, inner rod 70 is drawn in a distal direction, causing cam plate 190 to move distally as well. As plate 190 moves distally, pin 192 causes jaw 204 to move towards jaw 206 and slot 194 causes pin 196 on jaw 206 to move jaw 206 towards jaw 204. When handle 60 is in a fully closed position, jaws 206 and 204 will have moved into substantial parallel alignment and be ready for firing.

Figures 4, 5:
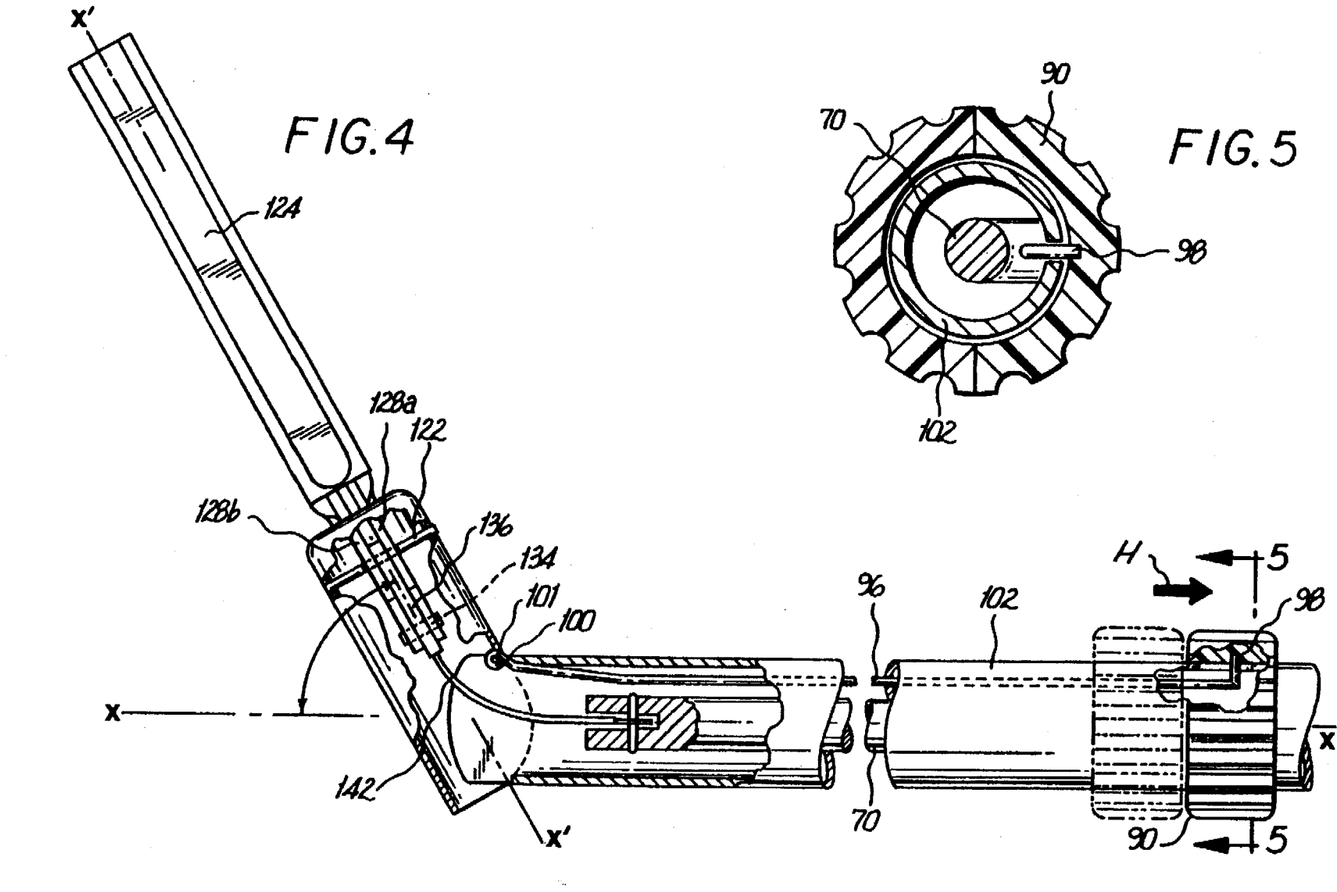
FIG. 4 illustrates a cut away plan view showing the jaws of FIG. 1 in an articulated position.
FIG. 5 illustrates a sectional view taken along lines 5—5 of FIG. 4.

Referring to FIGS. 4 and 5, articulation is achieved by pulling articulating knob 90 in a proximal direction (arrow H). This proximal movement causes articulating rod 96 to pull on articulating portion 116 at pin 101. When articulated, axis X'—X' of jaws 124 and articulated portion 116 moves away from axis X—X of the non articulating endoscopic portion of the instrument. At any jaw position the distal end of the instrument can be articulated and the jaws will open and close towards longitudinal jaw axis X'—X' of the instrument.

Figure 8:
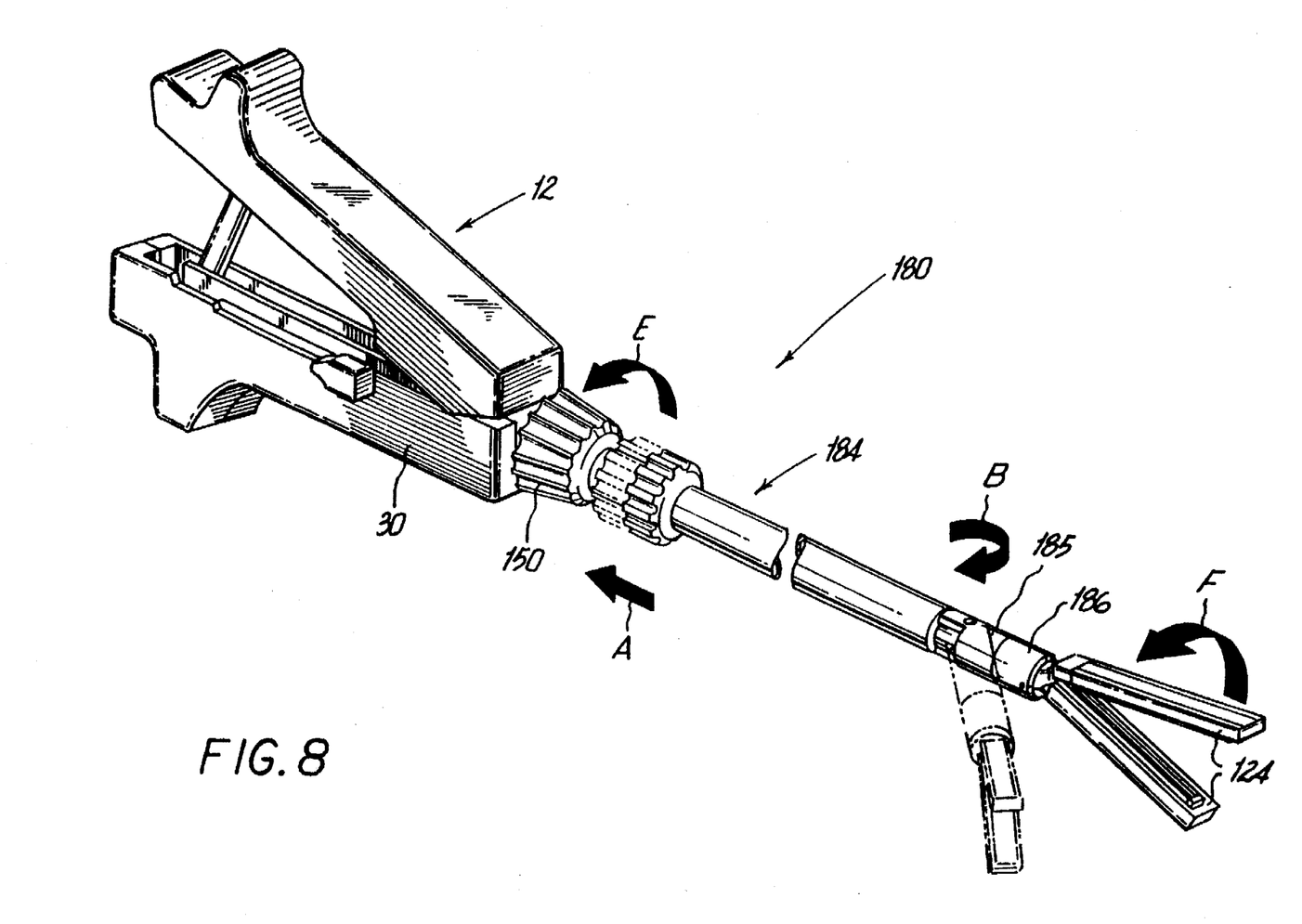
FIG. 8 illustrates a perspective view of an alternative embodiment of the present invention.
Figures 12, 13:
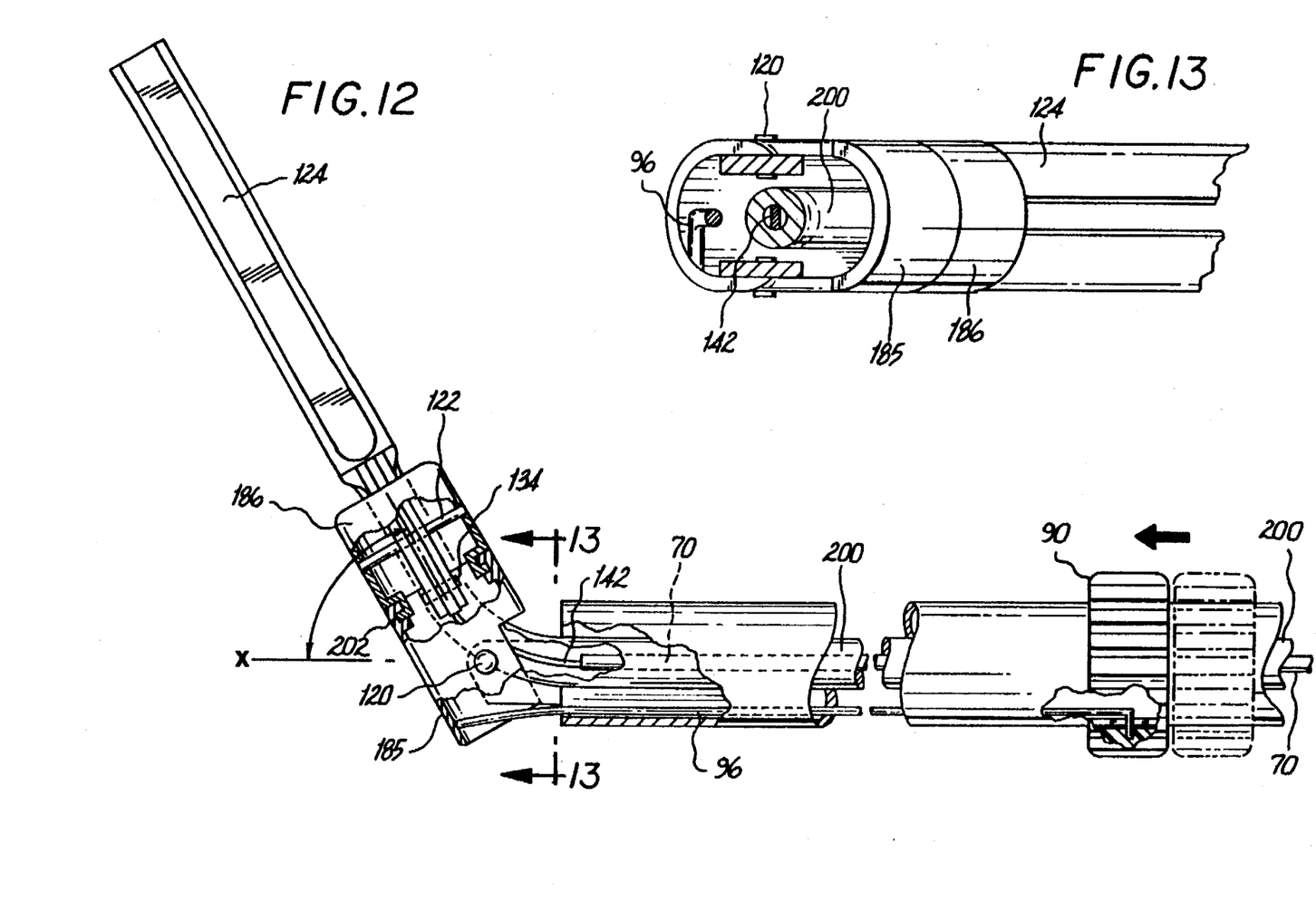
FIG. 12 illustrates a cut away plan view showing jaw articulation via a push rod.
FIG. 13 illustrates a sectional view taken along lines 13—13 of FIG. 12.

An alternative embodiment of the present invention is illustrated in FIGS. 8, 12 and 13. In this embodiment, rotation knob 150 causes the rotation of endoscopic articulation portion 186 and jaws 124, illustrated by arrows E and F, respectively, relative to endoscopic portions 184 and 185. This embodiment includes center rod cover sheath 200 (see FIG. 3) which provides means to translate rotation movement from knob 150 to the distal portion of the instrument. Referring to FIGS. 8 and 13, rotation of knob 150 causes sheath 200 to rotate, further causing distal articulating portion 186 and jaws 124 to rotate. Articulating portions 185 and 186 are rotatable with respect to each other by means of rotation joint 202. Both jaw cam pin 134 and jaw pivot pin 122 are located in rotatable articulation section 186. With sheath 200 secured to the proximal end of section 186, rotational movement bypasses the entire endoscopic portion proximal of joint 202. FIGS. 12 and 13 also show an alternative method of articulation. Here, distal movement of articulating knob 90 causes articulation rod 96 to push against portion 185, causing the distal end of the instrument to deflect away from axis X—X.

Figure 10:
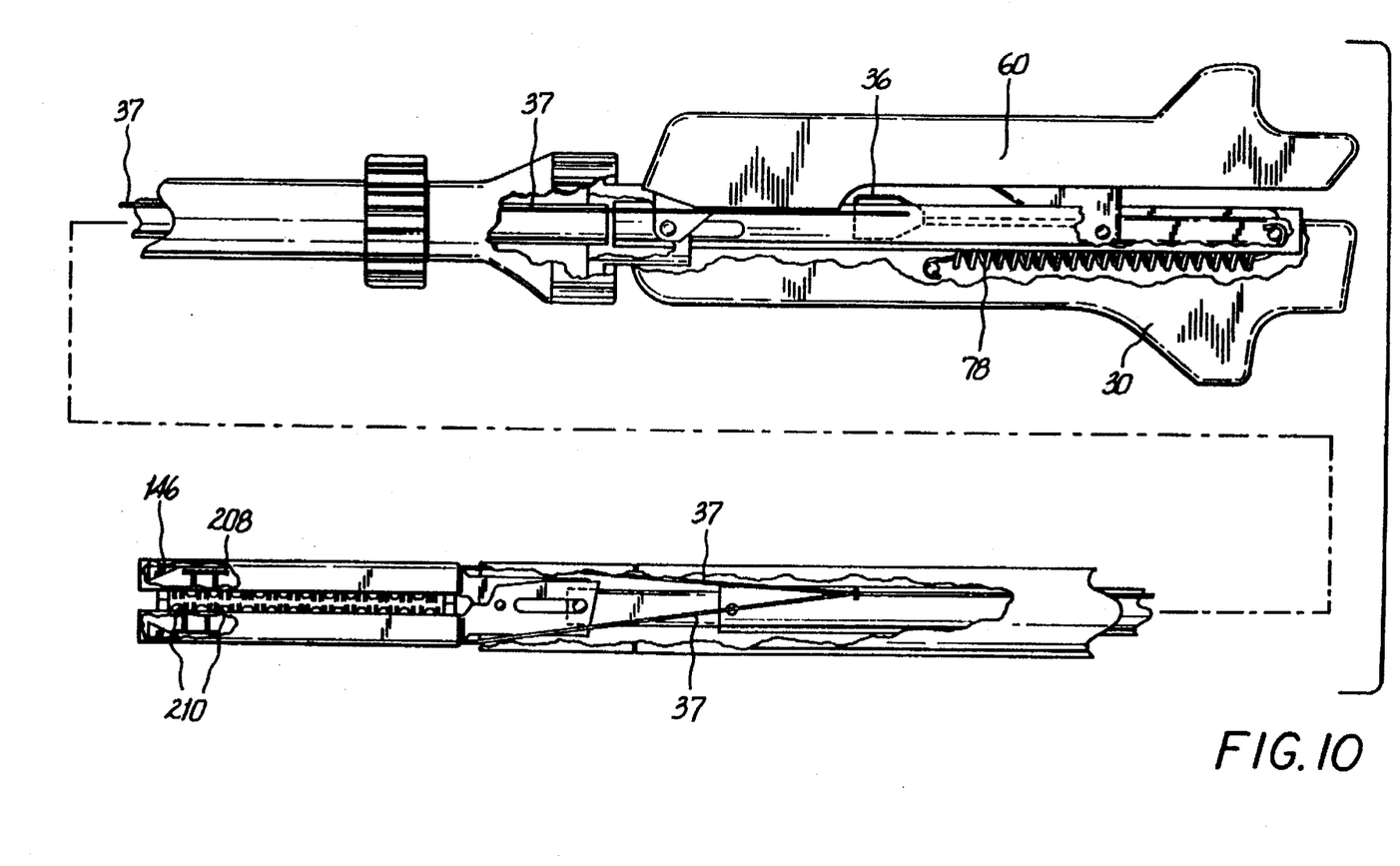
FIG. 10 illustrates the embodiment shown in FIG. 9 with the handle down and jaws closed.
Figure 11:
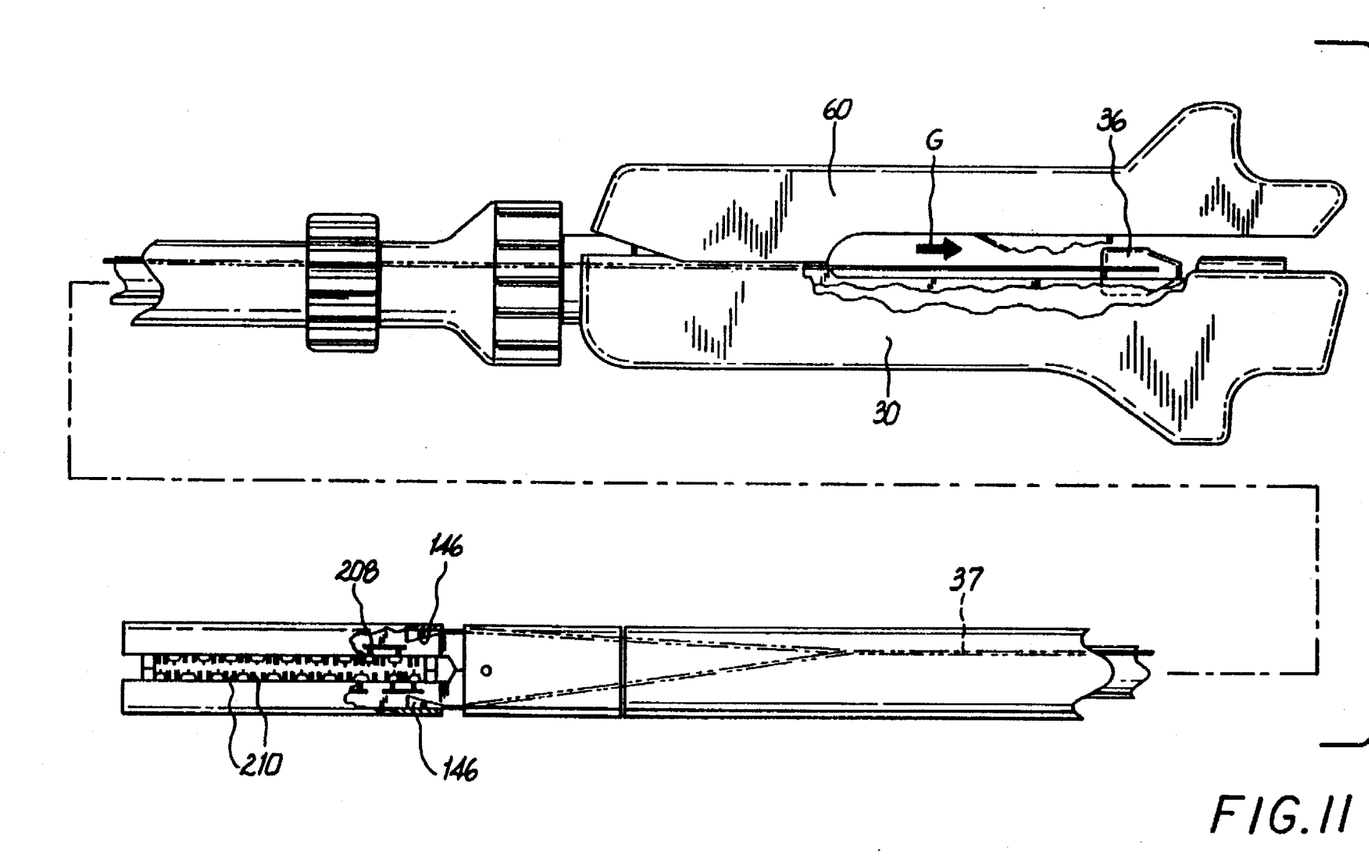
FIG. 11 illustrates the instrument of FIG. 10 after actuation of the fastener firing mechanism.

The firing mechanism of the present invention is best illustrated in FIGS. 10 and 11. Once the movable handle 60 and stationary handle 30 are brought in the closed position, the firing mechanism can be actuated. Firing button 36 can be drawn in a proximal direction (arrow G) thereby causing firing wires 37 and attached staple pusher cams 146 to be drawn proximally. Proximal movement of cams 146 causes staple pushers 208 to sequentially fire staples 210 from the jaws. Providing separate means for firing staples 210 from each jaw, such as a firing button secured to each firing wire (not shown), is considered within the scope of the invention.

Staples 210 are slidably mounted within the jaws or jaw cartridges and deformed without the use of an anvil upon ejection therefrom as disclosed in U.S. Pat. No. 4,821,939, which is incorporated herein by reference. Staples 210 are aligned such that their backspans are in substantial perpendicular alignment to the longitudinal axis X—X of the instrument when in the unarticulated position. As cams 146 are drawn across pushers 208, staples 210 are ejected towards axis X—X. It will be appreciated that when the instrument is in an articulated position, the staple backspans are in substantial perpendicular alignment to longitudinal axis X'—X' of the articulated jaws and are capable of being fired toward that longitudinal axis while articulated.

Figure 14:
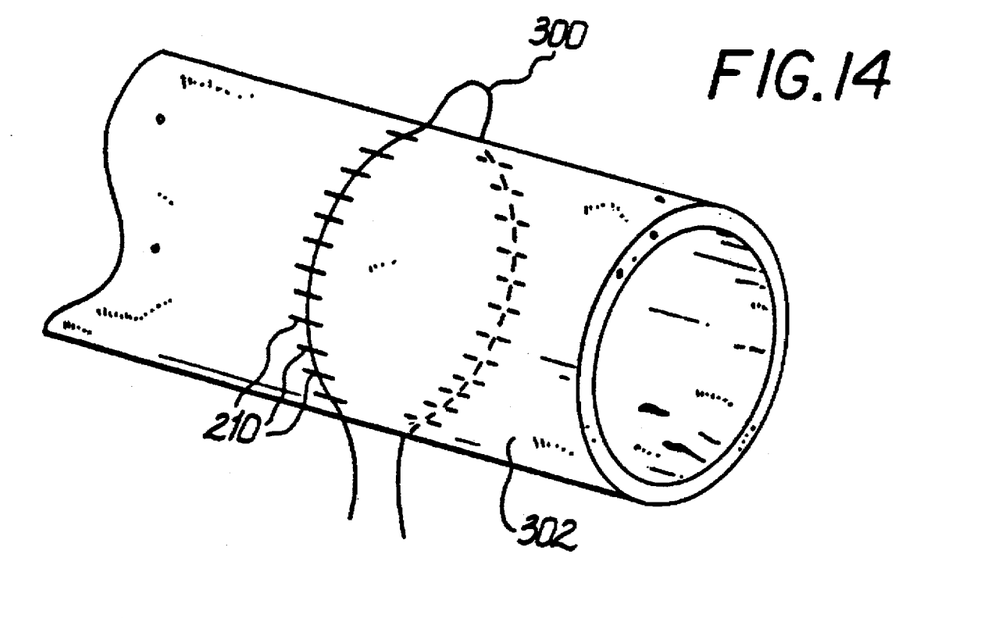
FIG. 14 illustrates a tubular section of tissue having a purse string applied thereto by the instrument of the present invention.

Referring to FIGS. 3, 6, 7 and 13, Suture 300 has two end portions, a body portion and is partially disposed adjacent tissue contacting surfaces 127 of fastener cartridges 125. Suture 300 is held in place by means of jaw stops 148 and 149 in a manner similar to that disclosed in U.S. Pat. No. 4,821,939. As shown in FIGS. 6 and 7, suture 300 loops back along jaws 124 with the two end portions terminating proximal of jaws 124. When applied, suture 300 is secured between the backspans of fasteners 210 (See FIGS. 10 and 11) and the tissue or organ to which the fasteners are applied (See FIG. 14). Any suture placement which allows the suture to be secured to body tissue by at least one fastener is considered to be within the scope of the present invention.

In operation, the instrument of the present invention is inserted through cannula with the handles and jaws in the closed position. Once within the abdominal cavity, movable handle 60 may be moved away from stationary handle 30, aided by spring 78, thereby causing center rod 70 to move in a distal direction, causing the jaws to open. Using the articulating and rotating mechanisms if desired, the organ or tissue to which the purse string is to be applied will be positioned between the jaws. The jaws may then be closed by bringing movable handle 60 towards stationary handle 30. With the tissue or organ disposed adjacent tissue contacting surfaces 125, the surgeon may then slide firing button 36 proximally to eject the staples into the tissue, thereby securing the suture. After firing, the surgeon will then open the handles and jaws as previously described to release the organ or tissue. Finally, by closing the handles and jaws, the surgeon may remove the instrument through the cannula.

While the invention has been particularly shown and described with reference to the preferred embodiments, it will be understood by those skilled in the art that various modifications in form and detail may be made therein without departing from the scope and spirit of the invention. For example, various elements, such as the jaw closing mechanism, the stapling firing mechanism and the articulation mechanism, can be modified while still performing the same or similar function. Accordingly, such modifications are to be considered within the scope of the invention as defined by the claims.

What is claimed is:

1. A surgical instrument comprising:

a handle portion having proximal and distal end portions and a longitudinal axis;

a pair of jaws extending generally longitudinally from the distal end portion, at least one of the jaws being movable relative to the longitudinal axis defined by the handle portion; and a plurality of fasteners disposed within at least one of said pair of jaws, wherein each fastener has a pair of legs joined by a backspan, the distal-most fastener backspan being oriented substantially perpendicular to the longitudinal axis of the handle portion and wherein each fastener is ejected in a direction generally towards said longitudinal axis when the instrument is fired.

2. The instrument of claim 1, wherein each jaw is movable between an open position and a closed position and wherein both jaws are in substantial parallel alignment with the longitudinal axis of the handle portion when in the closed position.

3. The instrument of claim 2, wherein each fastener has a pair of legs joined by a backspan and the fastener legs are generally oriented toward the longitudinal axis when the jaws are in the closed position.

4. The instrument of claim 1, further comprising anvilless means for deforming the fastener legs.

5. The instrument of claim 1, further comprising means for ejecting the fasteners from each jaw.

6. The instrument of claim 1, further comprising at least one cam member disposed in each jaw for sequentially ejecting the fasteners from each jaw.

* * * * *